US012268840B2

(12) United States Patent
Cook (10) Patent No.: US 12,268,840 B2
(45) Date of Patent: Apr. 8, 2025

(54) SYSTEM FOR DISPENSING FLUID

(71) Applicant: Proportion-Air, Inc., McCordsville, IN (US)

(72) Inventor: Daniel E. Cook, McCordsville, IN (US)

(73) Assignee: Proportion-Air, Inc, McCordsville, IN (US)

( * ) Notice: Subject to any disclaimer, the term of this patent is extended or adjusted under 35 U.S.C. 154(b) by 107 days.

(21) Appl. No.: 17/581,006

(22) Filed: Jan. 21, 2022

(65) Prior Publication Data

US 2022/0233766 A1    Jul. 28, 2022

Related U.S. Application Data

(60) Provisional application No. 63/140,262, filed on Jan. 22, 2021.

(51) Int. Cl.
| | | |
|---|---|---|
| A61M 5/14 | (2006.01) | |
| A61M 5/145 | (2006.01) | |
| A61M 5/148 | (2006.01) | |
| A61M 5/155 | (2006.01) | |
| A61M 5/168 | (2006.01) | |

(Continued)

(52) U.S. Cl.
CPC ...... *A61M 5/14593* (2013.01); *A61M 5/1483* (2013.01); *A61M 5/155* (2013.01); *A61M 5/16804* (2013.01); *A61M 5/16881* (2013.01); *A61J 1/10* (2013.01); *A61M 2005/1402* (2013.01); *A61M 2005/14204* (2013.01); *A61M 2205/3389* (2013.01); *A61M 2205/3561* (2013.01); *A61M 2205/3569* (2013.01); *A61M 2205/3576* (2013.01)

(58) Field of Classification Search
CPC ............ A61M 5/14593; A61M 5/1483; A61M 5/155; A61M 5/16804; A61M 5/16881; A61M 2005/1402; A61M 2005/14204; A61M 2205/3389; A61M 2205/3561; A61M 2205/3569; A61M 2205/3576; A61M 2205/0238; A61M 5/145; A61M 2005/14513; A61M 5/16877; A61J 1/10
See application file for complete search history.

(56) References Cited

U.S. PATENT DOCUMENTS

| | | |
|---|---|---|
| 3,640,277 A | 2/1972 | Adelberg |
| 4,337,769 A | 7/1982 | Olson |
| 5,207,645 A | 5/1993 | Ross et al. |

(Continued)

FOREIGN PATENT DOCUMENTS

KR    20190016746 A   *   2/2019

OTHER PUBLICATIONS

English translation of Baek (KR 20190016746) (Year: 2019).*

*Primary Examiner* — Courtney B Fredrickson
(74) *Attorney, Agent, or Firm* — Faegre Drinker Biddle & Reath LLP (57) ABSTRACT

Provided is a system for dispensing fluid. The system includes a housing defining a chamber; an inflatable bag disposed in the chamber and adapted to contain a fluid, the bag being in fluid communication with a flow path for flow of the fluid out of the bag; and a pressure source for inflating the bag to force the fluid from the bag to the flow path at a controlled rate. The bag inflates against an inner surface of the housing such that, prior to the bag being fully inflated, the fluid contained in the bag is forced from the bag at the controlled rate.

10 Claims, 7 Drawing Sheets

(51) Int. Cl.
  *A61J 1/10*    (2006.01)
  *A61M 5/142*   (2006.01)

(56) References Cited

U.S. PATENT DOCUMENTS

| | | |
|---|---|---|
| 5,348,539 A | 9/1994 | Herskowitz |
| 5,399,166 A | 3/1995 | Laing |
| 6,398,760 B1 | 6/2002 | Danby |
| 7,753,884 B2 | 7/2010 | Gallnbock |
| 8,267,894 B2 | 9/2012 | Nilsson et al. |
| 8,282,620 B2 | 10/2012 | Olson et al. |
| 8,641,671 B2 | 2/2014 | Michaud et al. |
| 9,067,012 B2 | 6/2015 | Chi et al. |
| 9,555,186 B2 | 1/2017 | Kruse |
| 9,597,449 B2 | 3/2017 | Imran |
| 9,662,439 B2 | 5/2017 | Rebergue et al. |
| 9,827,370 B2 | 11/2017 | Rebergue et al. |
| 2008/0319391 A1* | 12/2008 | Jackson .............. A61J 15/0069 604/404 |
| 2014/0276427 A1* | 9/2014 | Chi ...................... A61M 5/148 604/151 |
| 2017/0274143 A1* | 9/2017 | Sanchez, Jr. ............ A61F 9/007 |
| 2020/0215256 A1* | 7/2020 | Henry ................. A61M 3/0258 |
| 2020/0345930 A1* | 11/2020 | Puskás ............. A61M 5/16813 |

\* cited by examiner

SYSTEM FOR DISPENSING FLUID

CROSS-REFERENCE TO RELATED APPLICATIONS

This application claims the priority benefit of U.S. Provisional Patent Application No. 63/140,262, filed Jan. 22, 2021, which is incorporated herein by reference in its entirety.

TECHNICAL FIELD

The present disclosure relates generally to fluid dispensing systems and, more particularly, to fluid dispensing systems that utilize a pressure source to dispense fluid at a controlled rate.

BACKGROUND

Systems for dispensing fluids, particularly infusion systems for the intravenous (IV) delivery of fluids to a patient, are quite common in the medical field. In one approach, a bag containing a therapeutic fluid is inflated to exert pressure on the fluid and thereby force the fluid out of the bag. However, such an approach suffers from the bag being inflated and stretching, thereby resulting in variable pressure being exerted on the fluid in the bag based on the extent to which the bag has been inflated.

SUMMARY

The following introduces a selection of concepts in a simplified form in order to provide a foundational understanding of some aspects of the present disclosure. The following is not an extensive overview of the disclosure, and is not intended to identify key or critical elements of the disclosure or to delineate the scope of the disclosure. The following merely presents some of the concepts of the disclosure as a prelude to the more detailed description provided thereafter.

Embodiments of the present disclosure relate to systems for dispensing fluid. In one embodiment, the system includes a housing defining a chamber; an inflatable bag disposed in the chamber and adapted to contain a fluid, the bag being in fluid communication with a flow path for flow of the fluid out of the bag; and a pressure source for inflating the bag to force the fluid from the bag to the flow path at a controlled rate, wherein the bag inflates against an inner surface of the housing such that, prior to the bag being fully inflated, the fluid contained in the bag is forced from the bag at the controlled rate.

Further scope of applicability of the systems, apparatuses, and methods of the present disclosure will become apparent from the more detailed description given below. However, it should be understood that the following detailed description and specific examples, while indicating embodiments of the systems, apparatuses, and methods, are given by way of illustration only, since various changes and modifications within the spirit and scope of the concepts disclosed herein will become apparent to those skilled in the art from the following detailed description.

BRIEF DESCRIPTION OF THE DRAWINGS

Features of the present systems and techniques may be best understood from the following detailed description taken in conjunction with the accompanying drawings of which.

The headings provided herein are for convenience only and do not necessarily affect the scope or meaning of what is claimed in the present disclosure.

Embodiments of the present disclosure and their advantages are best understood by referring to the detailed description that follows. It should be appreciated that like reference numbers are used to identify like elements illustrated in one or more of the figures, wherein showings therein are for purposes of illustrating embodiments of the present disclosure and not for purposes of limiting the same.

DETAILED DESCRIPTION

Various examples and embodiments of the present disclosure will now be described. The following description provides specific details for a thorough understanding and enabling description of these examples. One of ordinary skill in the relevant art will understand, however, that one or more embodiments described herein may be practiced without many of these details. Likewise, one skilled in the relevant art will also understand that one or more embodiments of the present disclosure can include other features and/or functions not described in detail herein. Additionally, some well-known structures or functions may not be shown or described in detail below, so as to avoid unnecessarily obscuring the relevant description. It is originally intended to combine the configurations described in the various embodiments as appropriate. Also, one or more of the components in the embodiments disclosed herein may not be used.

Figure 1A:
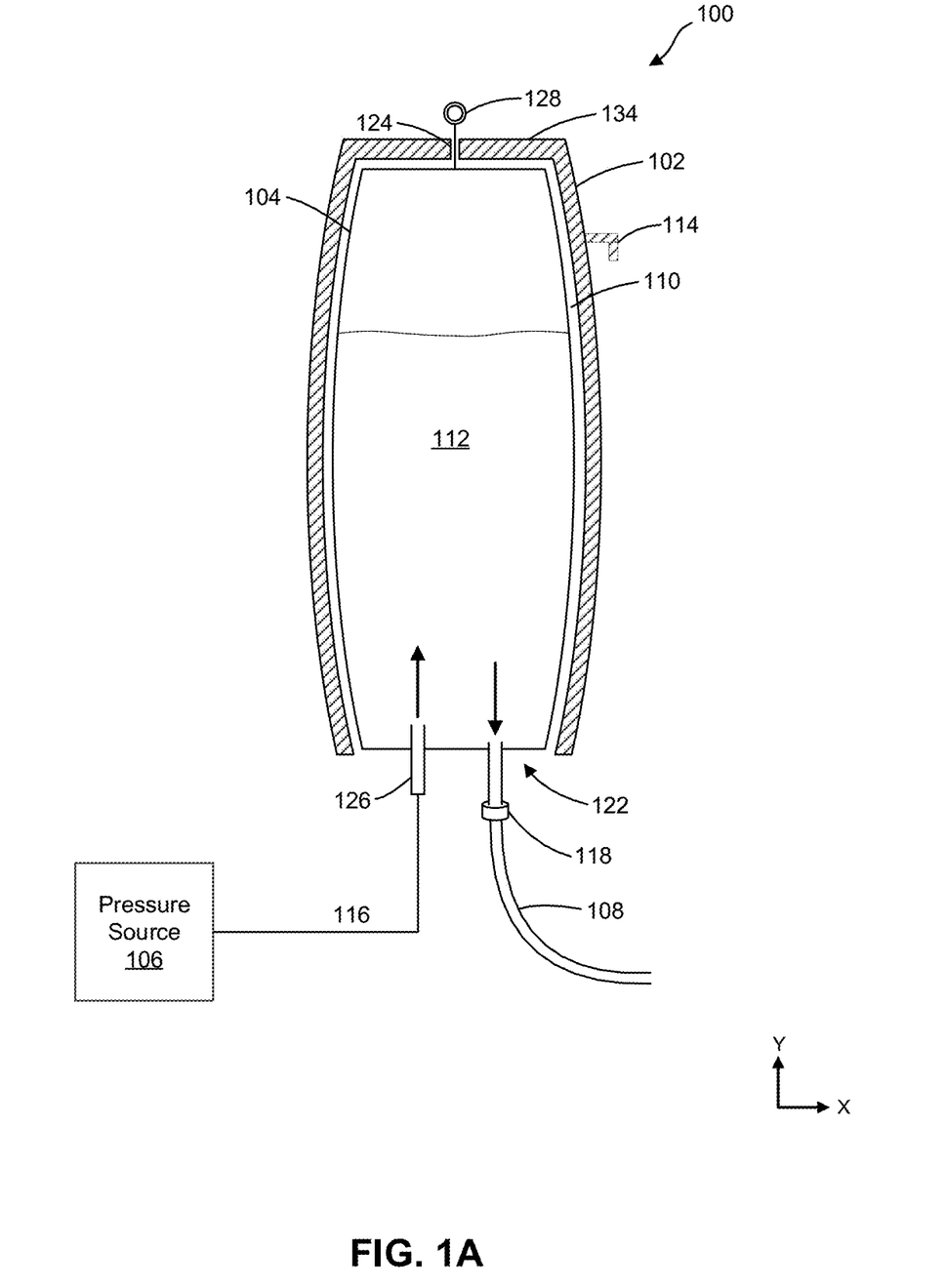
FIG. 1A shows a system for dispensing fluid according to an embodiment.

Turning to FIG. 1A, a system 100 for dispensing fluid according to an embodiment will now be described. As shown, the system 100 mainly includes a housing 102, a fluid bag 104, a pressure source 106, and a flow path 108. The housing 102 defines a chamber 110 within which the fluid bag 104 is disposed. In an embodiment, the chamber 110 is of a fixed volume. In another embodiment, the volume of the chamber 110 may be adjustable or may dynamically change while the fluid bag 104 is in use.

In an embodiment, the housing 102 is similar to a shell or container for the fluid bag 104. For example, the housing 102 acts as an exoskeleton for the fluid bag 104, giving support and rigidity to the fluid bag 104, which has none.

As illustrated in FIG. 1A, the housing 102 has an opening 122 at one end (e.g., the bottom end) to allow the fluid bag 104 to be inserted into the chamber 110, in an embodiment. In this manner, the housing 102 serves as a protective cover or case for the fluid bag 104. At the other end (e.g., top end) of the housing 102 opposite the opening 122 is an opening 124 formed in the top side 134 of the housing 102. The opening 124 formed in the top side 134 of the housing 102 serves to allow an attachment mechanism 128 of the fluid bag 104 to extend through the top side 134 of housing 102 from within the chamber 110. In an example, the attachment mechanism 128 of the fluid bag 104, which may be a ring, hook, or the like, may be inserted through the opening 124 in the top side 134 of the housing 102 for attachment to another apparatus or structure. For example, the attachment mechanism 128 of the fluid bag 104 may be used to hang or suspend the fluid bag 104 and housing 102 from a stationary or portable IV pole, a hospital bed, the interior of an ambulance, or some other structure or apparatus.

The housing 102 may be made of a non-compliant material or a rigid material including, for example, metal, plastic, fiberglass, or the like. The housing 102 can be any of a variety of shapes and sizes to accommodate the fluid bag 104 therein. For example, in one embodiment, the shape and size of the housing 102 emulates the shape of the fluid bag 104, such as illustrated in FIG. 1A. In an embodiment, the size of the housing 102 is only slightly larger than the size of the fluid bag 104, such that the housing 102 fits over the fluid bag 104 with a close fit. In one or more other embodiments, the housing 102 has a shape different from that illustrated in FIG. 1A.

Figure 1B:
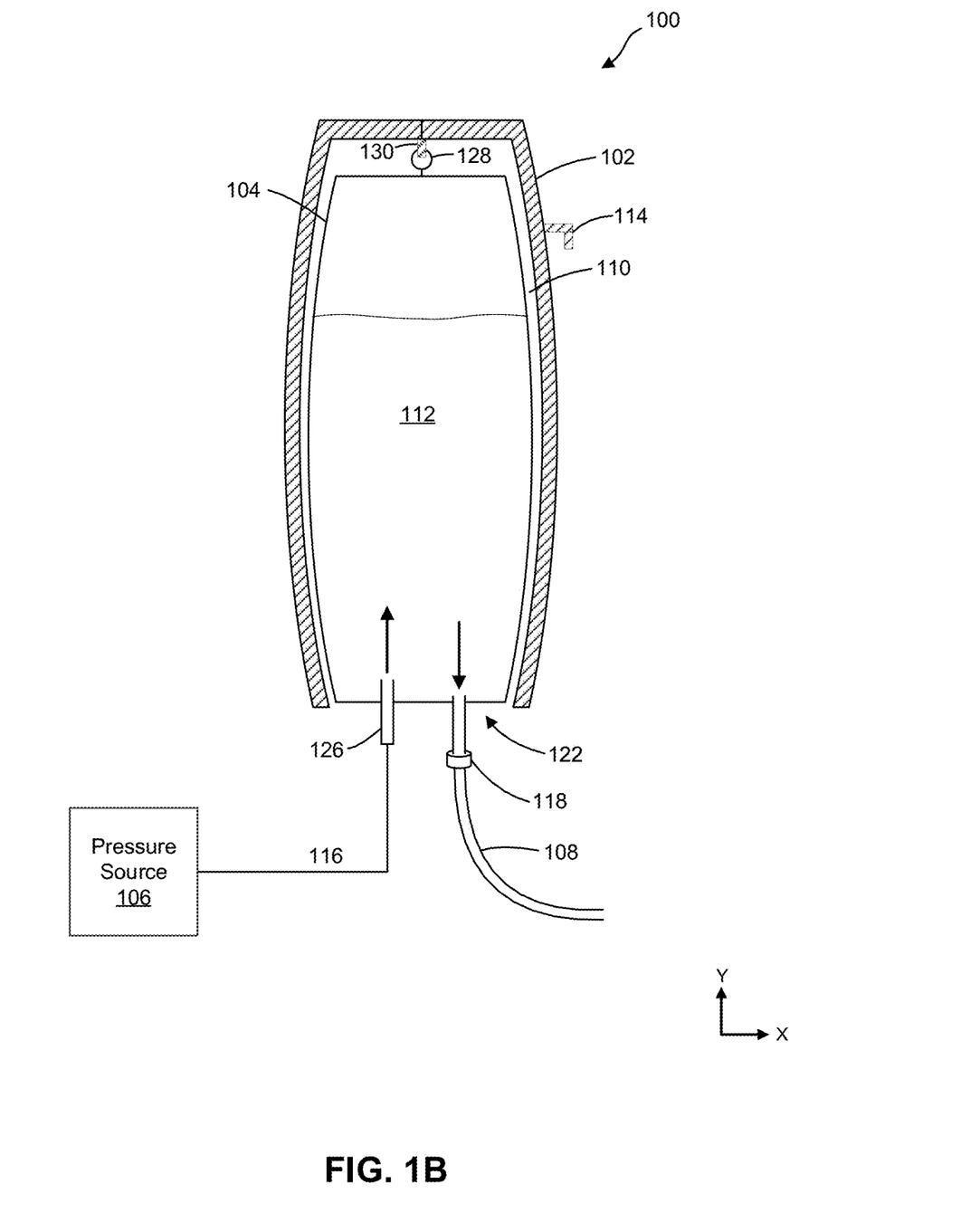
FIG. 1B shows a system for dispensing fluid according to another embodiment.
Figure 1C:
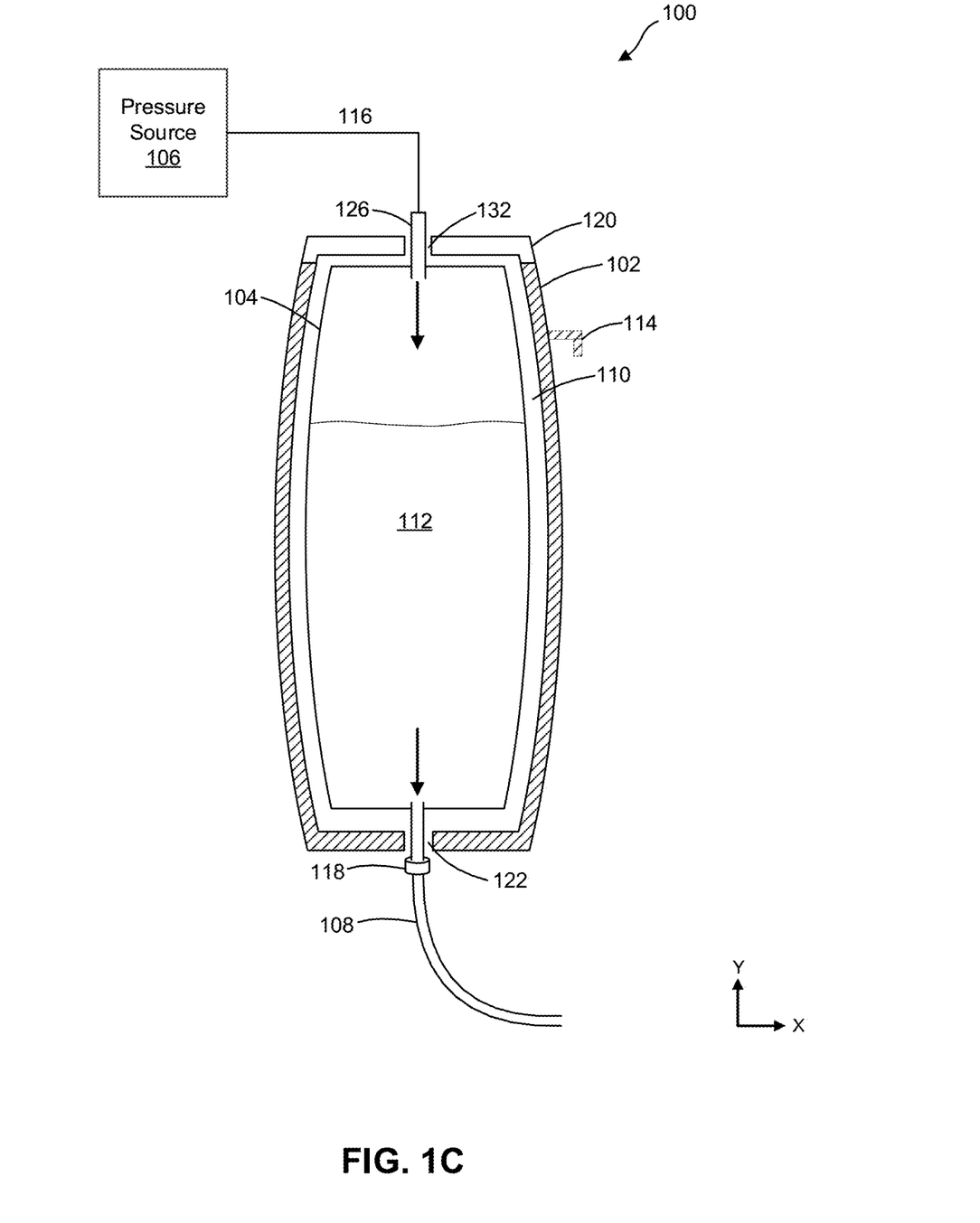
FIG. 1C shows a system for dispensing fluid according to another embodiment.
Figure 1D:
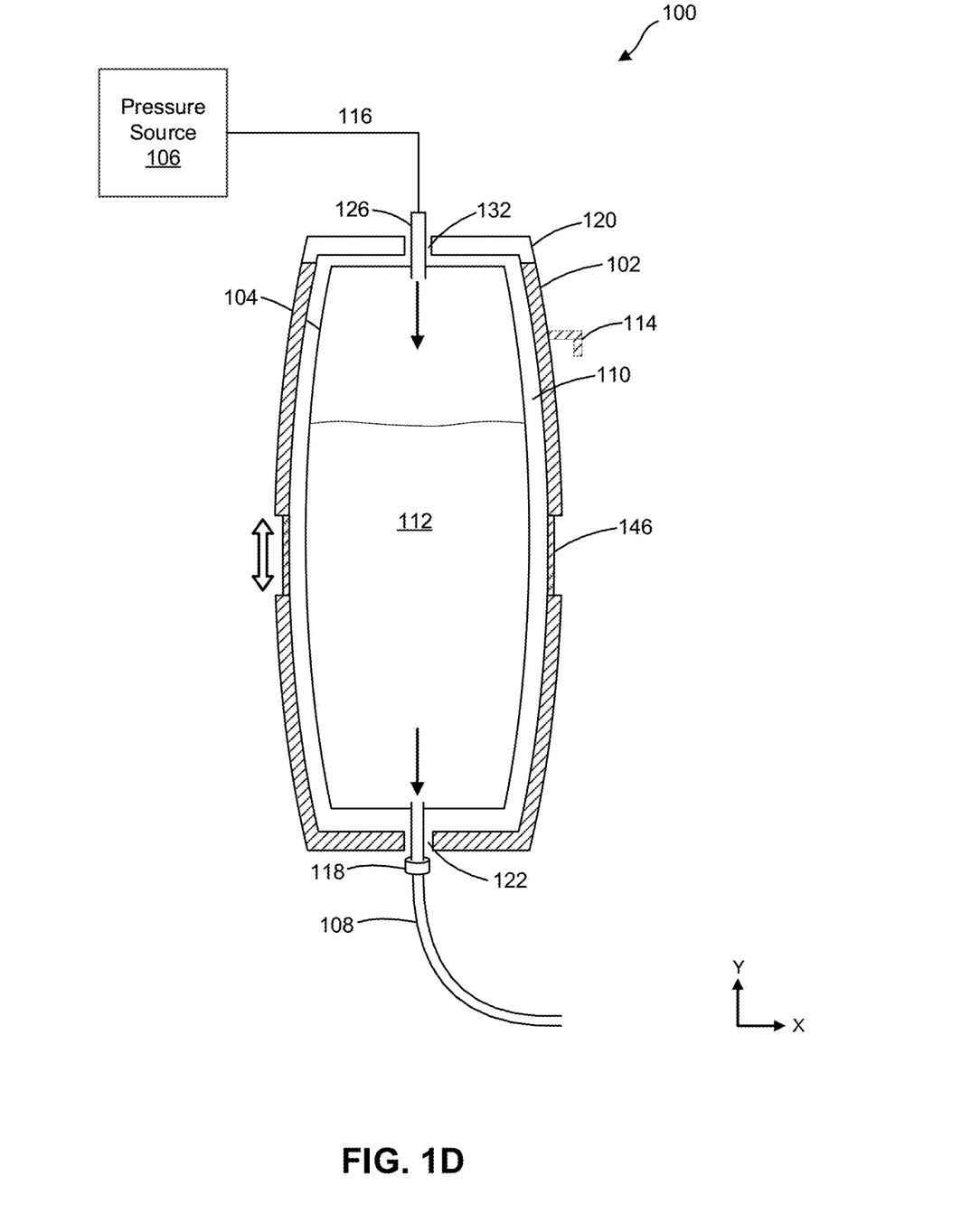
FIG. 1D shows a system for dispending fluid according to another embodiment.

In at least one embodiment, one or more dimensions of the housing 102 is adjustable such that fluid bags 104 of different sizes can be appropriately accommodated within the chamber 110 of the housing 102 in the intended manner. For example, FIG. 1D shows the housing 102 having an adjustable length (e.g., dimension corresponding to the Y-axis direction), in an embodiment. The housing 102 may have adjustable side portions 146, which can be expanded or reduced as necessary to accommodate larger or smaller fluid bags 104.

In an embodiment, the housing 102 may include an attachment mechanism 114 to enable the housing 102 to be attached to another apparatus or structure. For example, the housing 102 may be hung or otherwise suspended from a pole, shelf, bedpost, etc. The attachment mechanism 102 may be an extension of the housing 102 such that the attachment mechanism 114 is formed integral with the housing 102, in an embodiment. In one embodiment, the attachment mechanism 114 may be removably attached to the outside of the housing 102 (e.g., via one or more screws, as a clip-in attachment, etc.) so that the attachment mechanism 114 can be removed to accommodate a specific environment in which the system is used.

The fluid bag 104 is an inflatable bag adapted to contain a fluid 112. The fluid bag 104 is made of a flexible and impervious material known to those of ordinary skill in the art as being suitable for containing and dispensing fluids, including, for example, various polymers or plastics, polyolefin, ethylene vinyl acetate, glass, silicone glass, laminated aluminum foil, polyester, combinations thereof, or the like. The fluid bag 104 is connected to one end of a flow path 108 by a valve 118. The flow path 108 is preferably a tube such as a catheter, for example. The valve 118 that connects the fluid bag 104 to the one end of the flow path 108 may be any of a variety of types suitable to achieve the desired flow control out of the fluid bag 104.

The pressure source 106 provides pressurized air to the fluid bag 104 via a conduit 116 in order to inflate the fluid bag 104. For example, the pressure source 106 may be any suitable electro pressure controller or mechanical regulator known to those of ordinary skill in the art. In one embodiment, the conduit 116 attaches to a resilient inlet tube 126 extending from the same end of the fluid bag 104 as the valve 118 (FIGS. 1A and 1B). With reference to FIGS. 1C, in an embodiment, the valve 118 extends from the fluid bag 104 through a port 122 in the bottom of the housing 102, and the conduit 116 attaches to the resilient inlet tube 126 extending from the fluid bag 104 and passing through a port 132 in the top 120 of the housing 102.

In operation, the inflatable fluid bag 104 is inflated by air delivered from the pressure source 106 through the conduit 116 to the inflatable fluid bag 104. As the fluid bag 104 inflates against the inner surface of the housing 102, pressure is applied to the fluid bag 104 such that, prior to the fluid bag 104 being fully inflated, the fluid 112 contained in the fluid bag 104 is forced from the fluid bag 104 at a controlled rate. The fluid 112 is forced from the fluid bag 104 to the flow path 108 for delivery to a patient, for example. In one embodiment, a hydraulic pressure sensor (not shown) may be provided as part of the pressure source to monitor the pressure within the fluid bag 104.

It should be noted that the system 100 may be adapted for use with a variety of fluid bag shapes and/or configurations. For example, in some scenarios the entry and exit points to the fluid bag 104 may both be located on a same edge or side of the bag. For example, the fluid bag 104 may have a closed top edge such that the pressure port (e.g., inlet tube 126) and fluid delivery port (e.g., valve 118) are both located on a bottom edge of the fluid bag 104 (as in FIGS. 1A and 1B). In another example, the pressure port and fluid delivery port may be located on opposite edges of the fluid bag 104 (as in FIGS. 1C and 1D).

Turning to FIG. 1C, in at least one embodiment, the system 100 includes a removable top 120 that removably attaches to the housing 102. For example, the top 120 may twist or snap onto the housing 102, or may attach to the housing 102 via one or more buckles or clips (not shown). In the embodiment illustrated in FIG. 1C, the top 120 may include an opening 132 through which the inlet tube 126 passes from the conduit 116 to the fluid bag 104.

Figure 1E:
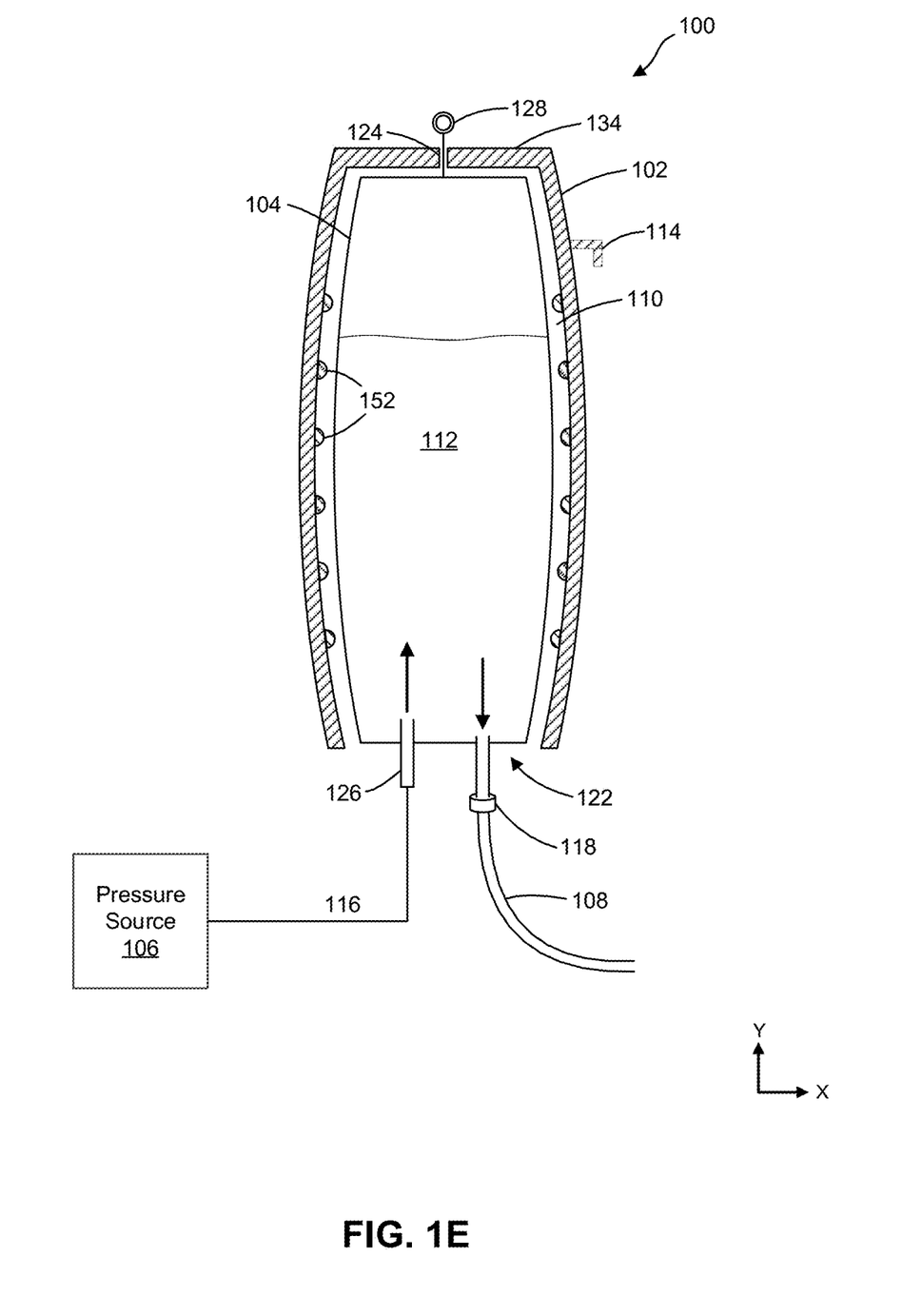
FIG. 1E shows a system for dispending fluid according to another embodiment.

FIG. 1E illustrates an embodiment in which a plurality of ribs 152 are formed on the inner surface of the housing 102 facing the fluid bag 104. The ribs 152 may provide additional points of pressure on the fluid bag 104 as it inflates against the inner surface of the housing 102. In one embodiment, the ribs 152 are spaced apart along the inner surface of the housing 102 with equal distance between adjacent ribs. In one or more other embodiments, the spacing between the ribs 152, the number of ribs 152, and/or the arrangement of the ribs 152 on the inner surface of the housing 102 may be different from what is shown in FIG. 1E. It should also be understood that while the ribs 152 shown in FIG. 1E have a shape resembling a semi-circle or half-moon, in other embodiments the ribs 152 may have a different shape and/or may be of a different size from what is illustrated.

Figure 2:
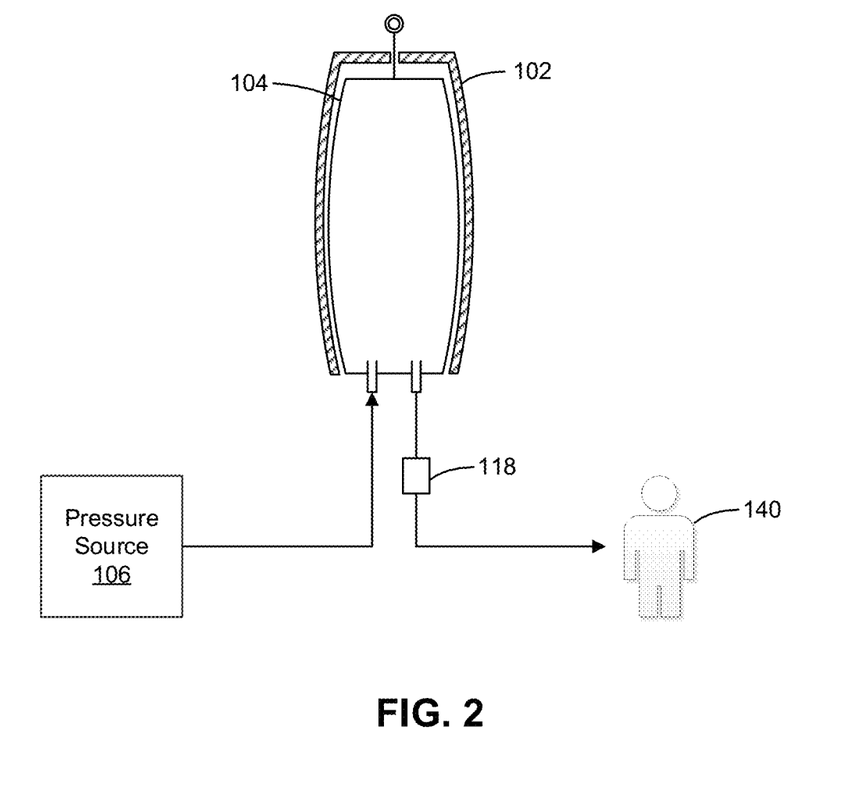
FIG. 2 shows a system for dispensing fluid to a patient according to an embodiment.
Figure 3:
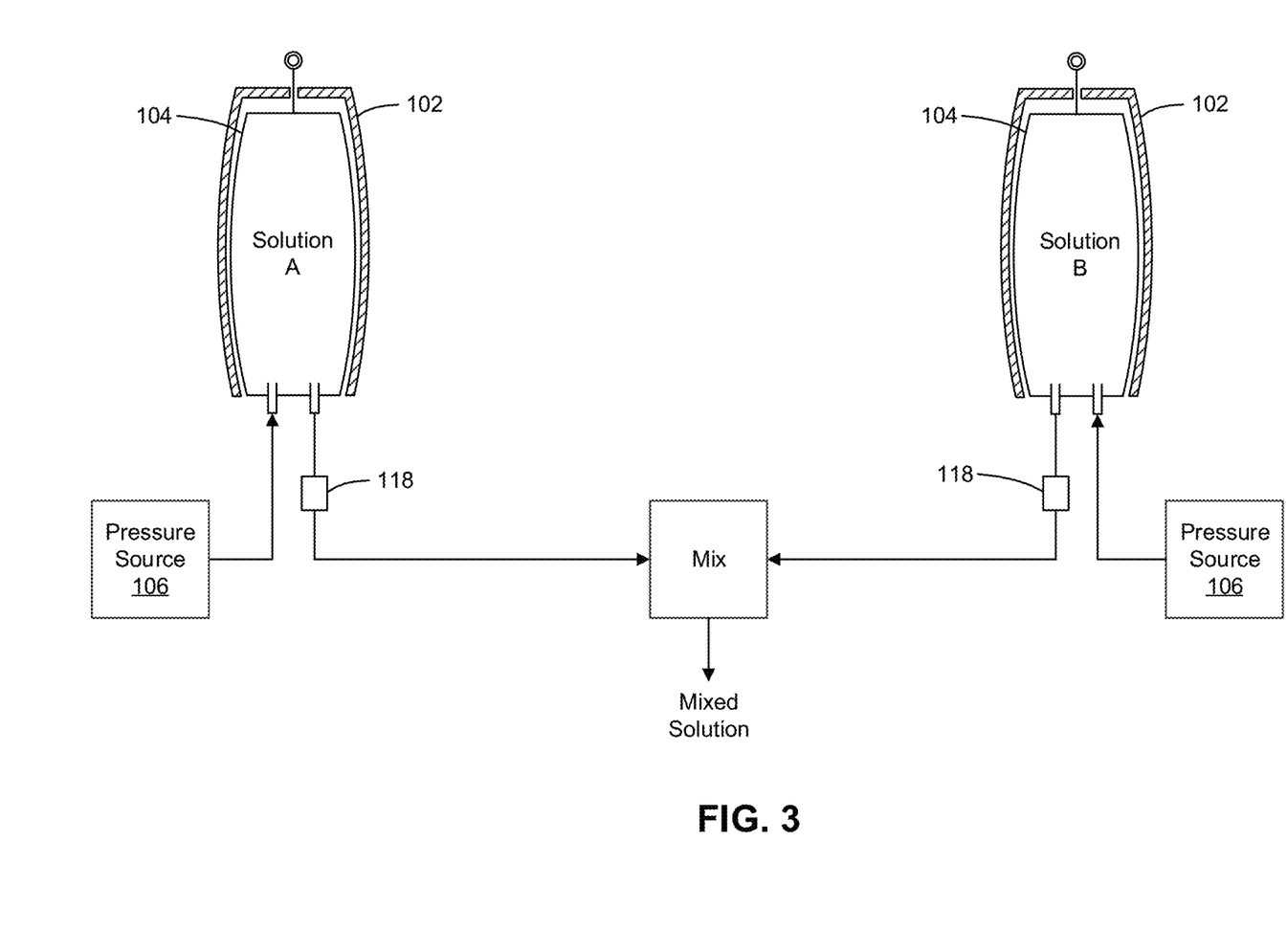
FIG. 3 shows a system for mixing multiple solutions according to an embodiment.

The systems and apparatuses disclosed herein may be useful in any of a variety of applications in the medical and pharmaceutical industries. FIGS. 2 and 3 illustrate example applications of the system 100. In one example, the medical industry uses saline solution for flushing during surgery. In another example, two solutions may be mixed to form a mixed solution.

For the purposes of promoting an understanding of the principles of the disclosure, reference has been made to the embodiments illustrated in the drawings, and specific language has been used to describe these embodiments. However, no limitation of the scope of the disclosure is intended by this specific language, and the disclosure should be construed to encompass all embodiments that would normally occur to one of ordinary skill in the art. Descriptions of features or aspects within each embodiment should typically be considered as available for other similar features or aspects in other embodiments unless stated otherwise. The terminology used herein is for the purpose of describing the particular embodiments and is not intended to be limiting of exemplary embodiments of the disclosure. In the description of the embodiments, certain detailed explanations of related art are omitted when it is deemed that they may unnecessarily obscure the essence of the disclosure.

The use of any and all examples, or exemplary language (e.g., "such as") provided herein, is intended merely to better illuminate the invention and does not pose a limitation on the scope of the invention unless otherwise claimed. Numerous modifications and adaptations will be readily apparent to those of ordinary skill in this art without departing from the scope of the invention as defined by the following claims. Therefore, the scope of the invention is defined not by the detailed description of the invention but by the following claims, and all differences within the scope will be construed as being included in the invention.

No item or component is essential to the practice of the invention unless the element is specifically described as "essential" or "critical". It will also be recognized that the terms "comprises," "comprising," "includes," "including," "has," and "having," as used herein, are specifically intended to be read as open-ended terms of art. The use of the terms "a" and "an" and "the" and similar referents in the context of describing the invention (especially in the context of the following claims) are to be construed to cover both the singular and the plural, unless the context clearly indicates otherwise. In addition, it should be understood that although the terms "first," "second," etc. may be used herein to describe various elements, these elements should not be limited by these terms, which are only used to distinguish one element from another. Furthermore, recitation of ranges of values herein are merely intended to serve as a shorthand method of referring individually to each separate value falling within the range, unless otherwise indicated herein, and each separate value is incorporated into the specification as if it were individually recited herein.

What is claimed is:

1. A system for dispensing fluid comprising:
    a housing defining a chamber;
    an inflatable bag disposed in the chamber and including an inner volume that contains a fluid, the inner volume of the bag being in fluid communication with a flow path for flow of the fluid out of the bag;
    a pressure source in fluid communication with the inner volume of the bag via an inlet for inflating the bag to force the fluid from the bag to the flow path at a controlled rate;
    wherein the bag inflates against an inner surface of the housing such that, prior to the bag being fully inflated, the fluid contained in the bag is forced from the bag at the controlled rate.

2. The system for dispensing fluid according to claim 1, wherein the housing is formed of a solid, non-flexible material.

3. The system for dispensing fluid according to claim 1, wherein a plurality of ribs are formed on the inner surface of the housing.

4. The system for dispensing fluid according to claim 3, wherein the plurality of ribs are spaced apart along the inner surface of the housing with equal distance between adjacent ribs.

5. The system for dispensing fluid according to claim 1, wherein one end of the housing is closed and the other end of the housing is open to receive the bag therein.

6. The system for dispensing fluid according to claim 1, wherein one end of the housing includes a removable top that removably attaches to the housing.

7. The system for dispensing fluid according to claim 1, wherein the housing includes a pair of side portions configured to be expandable to provide an adjustable length of the housing.

8. The system for dispensing fluid according to claim 1, wherein one end of the housing includes a port through which an inlet tube of the bag extends.

9. The system for dispensing fluid according to claim 1, wherein one end of the housing includes a port through which an outlet valve of the bag extends.

10. The system for dispensing fluid according to claim 1, wherein a first end of the housing includes a first port through which an inlet tube of the bag extends, and a second end of the housing includes a second port through which an outlet valve of the bag extends.

* * * * *